June 30, 1970 M. L. MEILLAND Plant Pat. 2,974
ROSE PLANT
Filed July 1, 1968
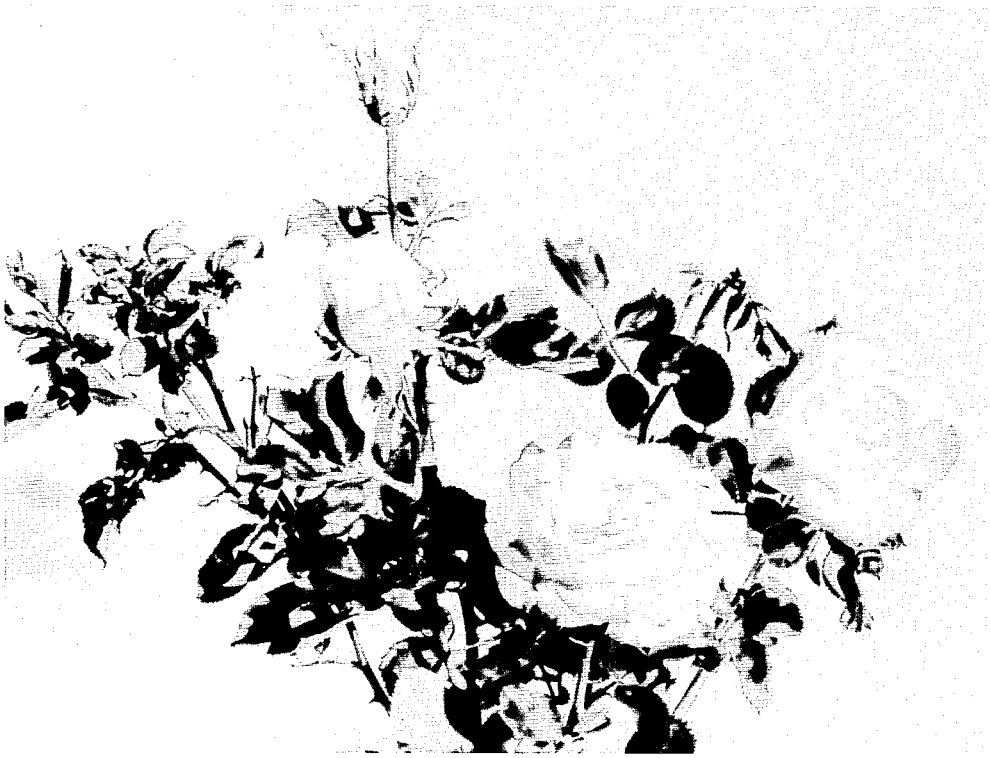

United States Patent Office

Plant Pat. 2,974
Patented June 30, 1970

2,974
ROSE PLANT

Marie Louise Meilland, Cap d'Antibes, France, assignor to The Conard-Pyle Company, West Grove, Pa., a corporation of Pennsylvania Filed July 1, 1968, Ser. No. 741,689
Int. Cl. A01h *5/00*
U.S. Cl. Plt.—11 1 Claim

ABSTRACT OF THE DISCLOSURE

A new and distinct variety of rose plant of the grandiflora class, originated by crossing Zambra with Suspense.

DESCRIPTION OF THE INVENTION

This invention relates to a new and distinct variety of rose plant of the grandiflora class which was originated by crossing Zambra with Suspense.

The primary objective of this breeding was to create a distinct variety of rose, different from all other known varieties of roses in several important characteristics.

When compared to its seed parent Zambra (Plant Pat. No. 2,140), this new rose has a larger flower, with many more petals and color tones in the petals, from scarlet red blending to a golden yellow, and a plant of more bushy upright growth covered more abundantly with more glossy foliage.

When compared to its pollen parent Suspense (Plant Pat. No. 1,944), this new rose produces many more blooms of novel color on a plant more vigorous and freely branched with foliage smaller and more abundant.

Asexual reproduction of my new variety as performed in West Grove, Pa.

The accompanying drawing shows typical specimens of the flowers and foliage of my new variety in different stages of development and as depicted in color as nearly true as is reasonably possible to make the same in a color illustration of this character.

The following is a detailed description of my new variety with color terminology in accordance with the horiticultural color chart of the Royal Horticultural Society.

Type: Hardy; tall bush, outdoor; seedling; garden decoration.
Class: Grandiflora.
Propagation: It does hold its distinguishing characteristics through succeeding propagations by budding.

THE FLOWER

Flowers borne: Single sometimes, but usually three; in a regular cluster; on normal, medium stems.
Quantity of bloom: Abundant outdoors.
Continuity: Continuous.
Fragrance: Slight; sweetbriar.
Bud:
*Peduncle.*—Medium long; medium heavy; erect; medium reddish green; also smooth; few hairs; brown.
*Before calyx breaks.*—Size—medium. Form—ovoid with a conspicuous neck; with foliaceous appendages on the surface of the bud; with medium, much cut foliaceous parts extending beyond the tip of the bud equal to ¼ to ½ of its length.
*As calyx breaks.*—Color—near Burnt Orange 014/1 shaded with near Currant Red 821/1.
*As first petal opens.*—Size—medium. Form—medium long, pointed. Color: outside—Currant Red 821 shaded with Mars Orange 013/1; Sulfur Yellow 1 at point of attachment; inside—brighter than Chrysanthemum Crimson 824; Aureolin 1 at very base of petal. Opening—it does open up well.

Bloom:
*Size when fully open.*—Medium, 3 to 3½ inches.
*Petalage.*—Very double; from 40 to 45 petals; arranged regularly.
*Form.*—High centered at first; remaining high centered; petals remaining at first loosely rolled outward; becoming later at maturity tightly rolled outward.
Petals: Thick; with inside velvety; outside satiny.
*Shape.*—Outer—obovate; with 3 notches. Intermediate—obovate; scalloped with apex pointed. Inner—obovate; with apex flat.
*Color.*—Colors may be modified by being penciled, blotched or shaded.

This description of a newly opened flower was made from a rose grown outdoors in June 1967, at West Grove, Pa.

*Color.*—Outer petal: outside surface—Majolica Yellow 09/2 sometimes shaded with Claret Rose 021; Sulphur Yellow 1 at point of attachment; Inside surface—deeper than Currant Red 821, shading to Mandarin Red 17/1 in veins and at lower quarter of petal; Aureolin 3 at very base of petal and point of attachment. Intermediate petal: outside surface—Majolica Yellow 09/1; Buttercup Yellow 5/1 at base of petal; very thin margin of Fire Red 15/1 at petal edges; inside surface—brighter than Cardinal Red 822; Aureolin 3 at base of petal. Inner petal: outside surface—Majolica Yellow 09/1; Canary Yellow 2 at base of petal; inside surface—Cardinal Red 822 shaded with Chrysanthemum Crimson 824; Aureolin 3 at base of petal.

This description was made from a rose that was open for three days, outdoors in June 1967, at West Grove, Pa.

*Color.*—Outer petal: outside surface—Aprical 609/2 splotched with between Delft Rose 020 and Delft Rose 020/1; Sulphur Yellow 1 at point of attachment; inside surface—between Chrysanthemum Crimson 824 and Turkey Red 721 mixing with Aureolin 3 at base of petal, becoming Aureolin 3 at point of attachment. Inner petal: outside surface—Cadmium Orange 8/2; Aureolin 3/1 at base of petal very lightly shaded with Marigold Orange 11/2 at petal margin; inside surface—Orient Red 819 deepening to darker than Orient Red 819 at petal edges; Lemon Yellow 4/1 at base of petal.
*General color effect.*—Newly opened flower—Bicolor Blood Red 820 with Yellow Ochre 07/2 on petal reverse. Three days open—Bicolor Orient Red 819; Orange Buff 507 on petal reverse.
*Behavior.*—Drop off cleanly.
*Flower longevity.*—On bush in garden 5 days in June; cut roses, grown outdoors, kept at living room temperatures 4 days in June.

REPRODUCTIVE ORGANS

Stamens: Medium; arranged regularly about pistils.
Filaments: Many; most with anthers; medium long. Color—deep yellow (general color term).
Anthers: Open at various times; medium large. Color—pale yellow (general color term). Seldom an anther fused with a petaloid.
Pollen: Moderate; gold.
Pistils: Medium.
Styles: Uneven; short to medium long; bunched.
Stigma: Yellow.
Ovaries: All enclosed in receptacle.

Hips: None observed.
Sepals: Permanent; medium long; spear shaped, recurved.
Seeds: None observed.

PLANT

Foliage:

*Leaves.*—Compound of 5; moderately abundant; medium; very heavy, glossy.

*Leaflets.*—Shape—oval with apex acute, base round, simply dentate.

*Color.* — Mature upper surface — Ivy Green 0001062/2. Under surface—Sage Green 000861/1, Young upper surface—Willow Green 000862 overlaid with Dahlia Purple 931/1. Under surface—Willow Green 0862/1 shaded with maroon (general color term).

*Rachis (the supporting stem of the compound leaf).*—Heavy. Upper side—hairy. Under side—sparsely prickly.

*Stipules.*—Moderately long; medium side; with medium points; turning out at an angle of more than 45°.

*Disease.*—Resistance comparable to the average variety growing under the same cultural conditions.

Growth:

*Habit.*—Bushy, upright.

*Growth.*—Free.

*Canes.*—Medium.

*Main stems.*—Dull; color—Lettuce Green 861/1 sometimes shaded with maroon (general color term). Prickles—several; color—near Dahlia Purple 931/1. Hairs—few; color—white (general color term).

*Branches.* — Dull; color — Lettuce Green 861/3. Prickles — several; color — near Dahlia Purple 931/1. Hairs—few; color—white, general color term).

*New shoots.*—Bright; color—near Pod Green 061. Prickles—several; color—Dahlia Purple 931/2; near Pod Green 061 at apex. Hairs—few; color—white (general color term).

I claim:

1. A new and distinct variety of rose plant of grandiflora class, substantially as herein shown and described, characterized particularly as to novelty by the unique combination of bud coloring of Currant Red shaded with Mars Orange and opening to a high centered fully double bloom of more than 40 petals deeper than Currant Red at the margin, shading to Mandarin Red and washed over Yellow, occasionally to the base of the petal; these blooms sometimes borne singly, but usually in clusters of three, continuously from late spring until fall on a plant that is freely branched and of medium height for its class, abundantly covered with Ivy Green foliage, exceptionally glossy, with disease resistance and winter hardiness comparable to other varieties of the class.

No references cited.

ROBERT E. BAGWILL, Primary Examiner